United States Patent
Melibari et al.

(10) Patent No.: US 10,889,533 B2
(45) Date of Patent: Jan. 12, 2021

(54) INLINE PROCESS TO MAKE ANTIFOULING AGENT CO-CATALYST FOR ETHYLENE OLIGOMERIZATION

(71) Applicant: Saudi Arabian Oil Company, Dhahran (SA)

(72) Inventors: Faisal M. Melibari, Thuwal (SA); Hussain M. Yami, Thuwal (SA); Sohel K. Saikh, Dhahran (SA); Zhonglin Zhang, Dhahran (SA); Wei Xu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/134,207

(22) Filed: Sep. 18, 2018

(65) Prior Publication Data

US 2019/0092707 A1  Mar. 28, 2019

Related U.S. Application Data

(60) Provisional application No. 62/561,736, filed on Sep. 22, 2017.

(51) Int. Cl.
  *C07C 2/30* (2006.01)
  *B01J 31/14* (2006.01)
  (Continued)

(52) U.S. Cl.
  CPC ............... *C07C 2/30* (2013.01); *B01J 31/143* (2013.01); *B01J 31/2208* (2013.01); *C07C 2/08* (2013.01);
  (Continued)

(58) Field of Classification Search
  None
  See application file for complete search history.

(56) References Cited

U.S. PATENT DOCUMENTS 2,738,151 A   3/1956  Herzog
3,686,350 A   8/1972  Ono et al.
(Continued)

FOREIGN PATENT DOCUMENTS

CN   101189270 A   5/2008
CN   102807632 A   12/2012
(Continued)

OTHER PUBLICATIONS

Office Action dated Dec. 13, 2018 pertaining to U.S. Appl. No. 15/181,923, filed Jun. 14, 2016.
(Continued)

*Primary Examiner* — In Suk C Bullock
*Assistant Examiner* — Alyssa L Cepluch
(74) *Attorney, Agent, or Firm* — Dinsmore & Shohl LLP

(57) ABSTRACT

A process for selectively producing 1-butene comprises combining at least one antifouling agent and at least one aluminum alkyl compound to form an antifouling feed stream, wherein bringing the antifouling agent into contact with the aluminum alkyl compound forms at least one antifouling agent co-catalyst in a first step. The antifouling agent co-catalyst may comprise a structure comprising a central aluminum molecule bound to an R1 group, an R2 group, and an R3 group. The process further comprises feeding the antifouling feed stream, a catalyst comprising at least one titanate compound, and ethylene into a reactor dimerize ethylene in a second step. The catalyst is fed as a stream separated from the antifouling feed stream. The feeds may be varied in real-time to adjust a ratio of the formed antifouling agent co-catalyst and residual aluminum alkyl compound or antifouling agent in the antifouling feed stream.

11 Claims, 2 Drawing Sheets

(51) Int. Cl.
*C07C 2/10* (2006.01)
*C07C 2/08* (2006.01)
*B01J 31/22* (2006.01)

(52) U.S. Cl.
CPC ............ *C07C 2/10* (2013.01); *C07C 2531/14* (2013.01); *C07C 2531/22* (2013.01)

(56) References Cited

U.S. PATENT DOCUMENTS

| | | | |
|---|---|---|---|
| 4,242,531 | A | 12/1980 | Carter |
| 4,484,016 | A | 11/1984 | Maschmeyer et al. |
| 4,528,415 | A | 7/1985 | Knudsen |
| 4,532,370 | A | 7/1985 | Le Quan et al. |
| 4,538,018 | A | 8/1985 | Carter |
| 4,606,854 | A | 8/1986 | Ozawa et al. |
| 4,615,998 | A | 10/1986 | Le Quan et al. |
| 5,376,706 | A | 12/1994 | Barsotti et al. |
| 5,728,912 | A | 3/1998 | Saqualain Haider Rizvi et al. |
| 5,792,895 | A | 8/1998 | Commereuc et al. |
| 5,877,376 | A | 3/1999 | Commereuc et al. |
| 6,184,428 | B1 | 2/2001 | Zahoor et al. |
| 7,122,497 | B1 | 10/2006 | Nagy et al. |
| 7,329,635 | B2 | 2/2008 | Dickakian et al. |
| 7,919,569 | B2 | 4/2011 | Xu et al. |
| 7,964,763 | B2 | 6/2011 | Dixon et al. |
| 8,227,653 | B2 | 7/2012 | Weber et al. |
| 8,252,871 | B2 | 8/2012 | Aliyev et al. |
| 10,280,125 | B2 * | 5/2019 | Sogo .................. C07C 2/32 |
| 2003/0109766 | A1 | 6/2003 | Commereuc et al. |
| 2013/0123443 | A1 * | 5/2013 | Siraux ................. C08F 210/16 526/64 |
| 2013/0303817 | A1 | 11/2013 | Shaik et al. |
| 2014/0088331 | A1 | 3/2014 | Rolland |
| 2015/0141605 | A1 | 5/2015 | Bradin |
| 2016/0367977 | A1 | 12/2016 | Shaikh et al. |
| 2017/0274356 | A1 * | 9/2017 | Cann ..................... B01J 37/16 |

FOREIGN PATENT DOCUMENTS

| | | | |
|---|---|---|---|
| CN | 103665201 A | 3/2014 | |
| CN | 103724149 A | 4/2014 | |
| EP | 135441 A1 | 3/1985 | |
| EP | 181954 A1 | 5/1986 | |
| EP | 221206 A1 | 5/1987 | |
| EP | 0352856 A1 | 1/1990 | |
| EP | 2738151 A1 | 6/2014 | |
| JP | H02-1990-088529 | 3/1990 | |
| WO | 2012013805 A1 | 2/2012 | |
| WO | 2015087303 A2 | 6/2015 | |
| WO | 2015087304 A2 | 6/2015 | |
| WO | 2015087305 A2 | 6/2015 | |
| WO | 2015118462 A1 | 8/2015 | |
| WO | WO-2015118462 A1 * | 8/2015 | .............. B01J 37/04 |
| WO | 2017120310 A1 | 7/2017 | |

OTHER PUBLICATIONS

International Search Report and Written Opinion pertaining to International Application No. PCT/US2018/051514 dated Jan. 3, 2019, 12 pages.
Office Action dated Jan. 11, 2019 pertaining to U.S. Appl. No. 15/393,865, filed Dec. 29, 2016.
Pietrzykowski et al., Reactions of methyl- and ethylaluminium compounds with alkoxyalcohols. The influence of alkoxyalcohol substituents on the structure of the complexes formed, Inorganic Chimica Acta 334, 2002, pp. 385-394, Elsevier.
ISR and Written Opinion pertaining to Application No. PCT/US2017/012299 dated Jun. 8, 2017.
ISR and Written Opinion pertaining to Application No. PCT/US2016/037366 dated Nov. 21, 2016.
Obrey et al., "A Lewis Base Promoted Alkyl/Alkoxid Ligand Redistribution: Reaction of [Me2Al(µ-OCPh3]2", Organometallics 20, pp. 5119-5124, 2001.
T. Mole, "Organoaluminium Compounds—XI. Reaction of Trialkylaluminiums with Dialkylaluminium Alkoxides", Australian Journal of Chemistry, Jan. 1, 1966, pp. 381-386.
Invitation to Pay Additional Search Fees and Partial Search Report Pertaining to Application No. PCTUS2016037366 dated Sep. 15, 2016.
Forestiere et al., "Oligomerization of Monoolefins by Homogenous Catalysts", Oil & Science and Technology-Review de l'Institute Francais du Petrole, pp. 663-664, vol. 64, No. 6, Nov. 2009.
P.D. Smith et al., "Ethylene dimerization over supported titanium alkoxides" Journal of Catalysis 105, pp. 187-198, 1987.
Al-Jaralla et al., "Part 1—Dimerization of Ethylene to Butene-1", Catalysis Today 14, pp. 1-124, 1992.
A. Hennico et al., "Butene-1 is made from ethylene", Hydrocarbon Processing, vol. 69:3 (1990)—Abstract Only.
Luann Farrell, "Developments in Linear Alpha Olefin (LAO) Comonomer Technologies for Polyethylene", Luann M. Farrell, ChemSystems PERP Program, May 2012.
Office Action dated Mar. 13, 2018 pertaining to U.S. Appl. No. 15/393,865.
Final Rejection dated Aug. 10, 2018 pertaining to U.S. Appl. No. 15/393,865.
International Search Report and Written Opinion dated Feb. 20, 2018 pertaining to International application No. PCT/US2017/064841.
Non-Final Office Action pertaining to U.S. Appl. No. 15/830,800 dated Oct. 19, 2018.
Office Action dated Nov. 6, 2019 pertaining to Chinese Patent Application No. 201680035981.0.
Final Office Action dated Feb. 5, 2020 pertaining to U.S. Appl. No. 15/181,923, filed Jun. 14, 2016, 12 pgs.
Office Action dated Sep. 4, 2019 pertaining to U.S. Appl. No. 15/181,923, filed Jun. 14, 2016, 13 pgs.
Office Action dated May 10, 2019 pertaining to U.S. Appl. No. 15/181,923, filed Jun. 14, 2016, 16 pgs.
Office Action dated Jun. 6, 2019 pertaining to U.S. Appl. No. 15/393,865, filed Dec. 29, 2016, 14 pgs.
Extended European Search Report dated Dec. 20, 2019 pertaining to European Patent Application No. 19188473.3.
Examination Report pertaining to India Application No. 201837025980 dated Apr. 27, 2020, 6 pgs.
Final Office Action dated Feb. 28, 2020 pertaining to U.S. Appl. No. 15/393,865, filed Dec. 29, 2016, 32 pgs.
Office Action pertaining to RU2018128919 dated Feb. 27, 2020, 10 pgs.
Office Action dated Jul. 8, 2020 pertaining to Japanese Patent Application No. 2017-565808.
Office Action dated Aug. 10, 2020 pertaining to Singapore Patent Application No. 11201805653U.
U.S. Office Action dated Aug. 20, 2020 pertaining to U.S. Appl. No. 15/181,923, filed Jun. 14, 2016, 23 pgs.

* cited by examiner

INLINE PROCESS TO MAKE ANTIFOULING AGENT CO-CATALYST FOR ETHYLENE OLIGOMERIZATION

CROSS-REFERENCE TO RELATED APPLICATIONS

This application claims the benefit of U.S. Provisional Application Ser. No. 62/561,736 filed Sep. 22, 2017, incorporated herein by reference.

BACKGROUND

Field

Embodiments of the present disclosure generally relate to processes and catalyst systems used in ethylene oligomerization and, more specifically, relate to processes and antifouling catalyst systems used in ethylene oligomerization which reduce undesired polymerization.

Technical Background

1-Butene and 1-hexene are important petrochemicals, especially for the productions of polyethylene. The reaction of ethylene and other alpha-olefins, especially 1-butene and 1-hexene, forms various grades of linear low density polyethylene (LLDPE), a useful commercial polymer. A source of 1-butene is the butene fraction from the effluent of a hydrocarbon cracker, such as a steam cracker or fluidized catalytic cracker. However, the process for isolating 1-butene from such an effluent requires several difficult process steps that may make the process undesirable.

Several commercial processes selectively oligomerize ethylene into alpha-olefins such as 1-butene and 1-hexene. A commercially successful dimerization process is the Alphabutol™ Process, developed by the Institute Francais du Petrole (IFP), described in A. Forestiere, et al., "Oligomerization of Monoolefins by Homogenous Catalysts", Oil & Science and Technology—Review de l'Institute Francais du Petrole, pages 663-664 (Volume 64, Number 6, November 2009). This process uses a bubble-point reactor that contains 1-butene as a process fluid to oligomerize ethylene selectively into 1-butene.

There is a known problem with oligomerization systems: polymer formation. Long residence times and poor heat removal from the highly exothermic reactions lead to the formation of polyethylene-based residues. A side effect of chronic fouling is increasingly frequent process shutdowns and higher maintenance costs for removing adhered polymer residues. Polymer residues may build layer upon layer and eventually close off openings and ports in locations with fluid flow. Additionally, a polymer coating along the wall of a reactor may act as an insulator, which may negatively affect heat transfer to the reactor system. Polymer deposits may also collect debris that can poison the reaction process.

An especially troublesome issue is the formation of "hot spots". A hot spot is an area where external cooling is ineffective and catalyst activity is high. It represents a loss of process control. A hot spot can be caused in an area of collected polymer that includes catalytically active material that fosters side-reactions, including polymerization. If left unchecked, the hot spot can eventually lead to a process shutdown due to the loss of cooling capacity, a runaway polymerization reaction, or both.

SUMMARY

There is a continual need for effective reactor systems and methods to prevent polymeric fouling on reactor system walls and tubes while maintaining the desired oligomerization rate and selectivity to form desired reaction products.

According to one embodiment, a process for selectively producing 1-butene is provided. The process includes a first step of combining at least one antifouling agent and at least one aluminum alkyl compound to form an antifouling feed stream. Bringing the at least one antifouling agent into contact with the at least one aluminum alkyl compound forms at least one antifouling compound including a central aluminum molecule bound to an R1 group, bound to an R2 group, and bound to an R3 group or derivatives thereerof. An atom existing in the chemical groups R1, R2, or R3 optionally binds to the aluminum atom to form a chelate ring. The process includes a second step of feeding the antifouling feed stream, a catalyst comprising at least one titanate compound, and ethylene into a reactor to dimerize ethylene. The catalyst comprising the at least one titanate compound is fed as a stream separated from the antifouling feed stream. The molar ratio of the at least one antifouling agent and the at least one aluminum alkyl compound may be varied in real-time via an inline mixer to adjust a ratio of the formed antifouling agent co-catalyst and residual aluminum alkyl compound in the antifouling feed stream.

Additional features and advantages of the embodiments described herein will be set forth in the detailed description which follows, and in part will be readily apparent to those skilled in the art from that description or recognized by practicing the embodiments described, including the detailed description which subsequently follows, and the claims.

DEFINITIONS

Figure 1:
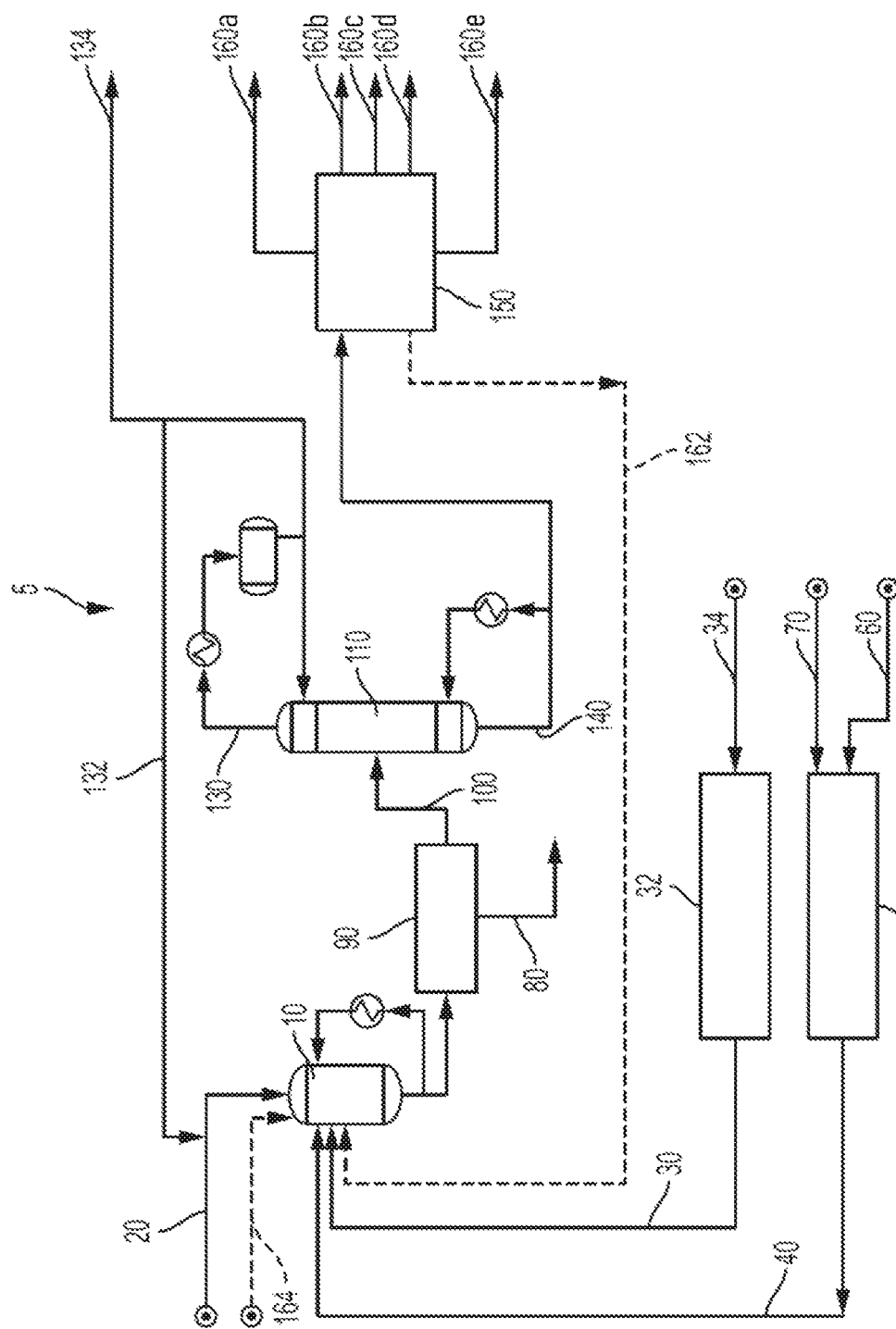
FIG. 1 is a schematic illustration of a generalized improved ethylene oligomerization process with an antifouling agent co-catalyst (ATA co-catalyst) injection system in accordance with one or more embodiments of the present disclosure.

In this disclosure, the term "antifouling agent" is used to refer to agents which are added to the process, more specifically to the AFA co-catalyst preparation section in FIG. 1, to prevent the polymer fouling and to improve polymer removability.

In this disclosure, the term "AFA co-catalyst" and the unabbreviated "antifouling agent co-catalyst" is used to refer to aluminum compounds which are newly formed in the AFA co-catalyst preparation section in FIG. 1 by the reaction of the antifouling agents and co-catalyst.

DETAILED DESCRIPTION

One or more embodiments of the present disclosure are directed to reactor and catalyst systems which may be utilized in promoting ethylene oligomerization, such as the dimerization of ethylene to form 1-butene, while reducing reactor fouling caused by undesired polymerization. These catalyst systems are sometimes referred to in this disclosure as "antifouling ethylene oligomerization catalyst systems" or "antifouling catalyst systems". The antifouling catalyst systems described may comprise at least one titanium based catalyst, at least one co-catalyst, and at least one antifouling agent or derivative thereof. Embodiments of the antifouling catalyst systems described may comprise at least one titanate compound, at least one aluminum alkyl compound as the co-catalyst, and at least one antifouling agent or derivative thereof. The antifouling catalyst systems may further comprise one or more ether compounds. The antifouling catalyst systems may be used to selectively oligomerize ethylene to produce 1-butene and other higher α-olefins, while reducing undesirable polymerization, sometimes referred to in this disclosure as "fouling". For example, reactor fouling may occur due to the formation of solid polyethylene-based residues which may reduce fluid flow and partially or fully block fluids in a reactor system from flowing at a desired rate. It should be understood that the "antifouling ethylene oligomerization catalyst systems" or "antifouling catalyst systems" described may not completely eliminate fouling during a reaction. However, these catalyst systems reduce fouling and make any formed polymer easier to remove as compared with catalyst systems which do not include an antifouling agent as described in the present disclosure. Also, it should be understood that while the catalyst systems of the present disclosure may be useful in ethylene oligomerization reactions, such as ethylene dimerization to form 1-butene, they may also be useful for the catalysis of other chemical reaction, and the antifouling catalyst systems described in this disclosure should not be considered limited in their use to the dimerization of ethylene to 1-butene.

According to embodiments of the present disclosure, 1-butene may be produced through ethylene dimerization. According to the method for 1-butene production, ethylene may be brought into contact with the antifouling catalyst system to dimerize ethylene to form 1-butene. In one or more embodiments, ethylene and an antifouling catalyst system are supplied to a reactor and mixed. The reaction may be performed as a batch reaction or as a continuous process reaction, such as a continuous stir tank reactor process. According to embodiments, the pressure in the reactor may be from 5 bar to 100 bar, and the reactor temperature may be from 30 degrees Celsius (° C.) to 180° C. However, process conditions outside of these ranges are contemplated, especially in view of the specific design of the reactor system and concentrations of the reactants and catalysts.

Figure 2:
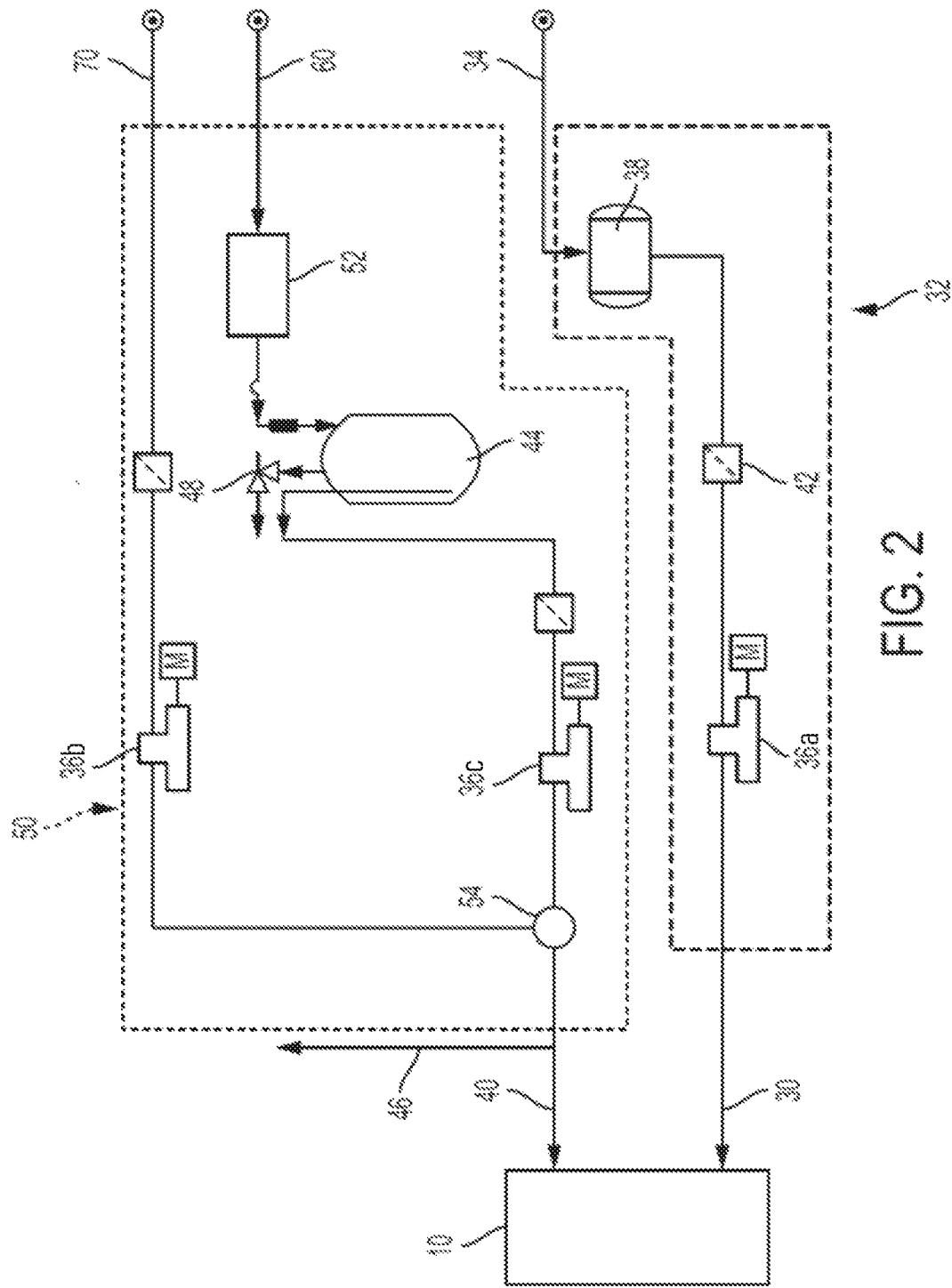
FIG. 2 is a schematic of a catalyst feed stream into a reactor and an antifouling feed stream into the reactor in accordance with one or more embodiments of the present disclosure.

In operation an AFA co-catalyst injection system 5 provides a catalyst and an AFA co-catalyst to the reactor during ethylene oligomerization. The AFA co-catalyst is formed from a co-catalyst and an antifouling agent and the catalyst generally comprises one or more titanate compounds. The combination of the AFA co-catalyst and the catalyst forms the antifouling catalyst system. With reference to FIG. 1, a schematic of the generalized improved ethylene oligomerization process with the AFA co-catalyst injection system 5 is shown. Ethylene is fed into a reactor 10 as an ethylene feed 20 where the catalyzed oligomerization of the ethylene to 1-butene and other higher α-olefins occurs. Additionally, the reactor 10 has separate inputs for a catalyst stream 30 comprising the catalyst and an antifouling feed stream 40 comprising the AFA co-catalyst. The antifouling feed stream 40 comprises the mixture of the at least one antifouling agent and at least one co-catalyst, the co-catalyst comprising at least one aluminum alkyl compound. As illustrated in FIGS. 1 and 2, the mixture is prepared in the AFA co-catalyst preparation section by combining the antifouling agent provided in an antifouling agent make-up stream 60 and the at least one co-catalyst provided in a co-catalyst make-up stream 70 in an appropriate ratio. The separate inputs allow interaction between the catalyst and the AFA co-catalyst to occur within the reactor 10. Additionally, the catalyst stream 30 is provided to the reactor 10 from a catalyst preparation section 32 as illustrated in FIGS. 1 and 2, the catalyst preparation section 32 fed from a catalyst make-up stream 34. Subsequent to the reactor 10, the spent catalyst 80 is separated from the stream exiting the reactor 10 in a catalyst removal section 90. The remaining reactor exit stream after the spent catalyst removal serves as a process stream 100 being provided to an ethylene recycle column 110. The ethylene recycle column 110 separates residual ethylene 130 from the process stream 100 for recycle as an ethylene recycle stream 132 back to the reactor 10 for oligomerization or to be purged from the AFA co-catalyst injection system 5 as an ethylene purge stream 134 and utilized as fuel. The non-ethylene stream exiting the ethylene recycle column 110 is further provided as a product process stream 140 to a distillation section 150 for further separation of components. For example, the distillation section 150 may separate the product process stream 140 into a plurality of product streams 160a through 160e including 1-butene, 1-hexene, 1-octene, 1-decene and a heavy cut, respectively. This separation may be achieved in accordance with any standard techniques known now or in the future to one having skill in the art. It will be appreciated that separation of the product process stream 140 into various components may be adjusted based on the make-up of the product process stream 140 and the particular chemical species or species within the product process stream 140 desired for further use or collection. The distillation section 150 may also separate solvents from the product process stream 140 which may be recycled back to the reaction 10 as a solvent recycle stream 162. Solvents may also be introduced to the reactor 10 directly with a solvent makeup stream 164.

With reference to FIG. 2, a schematic of an embodiment of the catalyst feed stream 30 into the reactor 10 is provided. The catalyst is provided from a catalyst source to the reactor 10 by a first pump 36a or other locomotion means. In at least one embodiment, a catalyst storage drum 38 is provided which provides a reservoir of catalyst for supply to the reactor 10 on an on-demand basis. The catalyst storage drum 38 maintains a reservoir of catalyst for supply to the reactor 10 and is resupplied from the catalyst make-up stream 34. Further, in embodiments, a filter 42 is provided in-line in the conduit connecting the catalyst source or catalyst storage drum 38 to the reactor 10. The filter 42 provides removal of particulates or other foreign components from the catalyst stream.

Throughout this disclosure the discussed catalyst comprises at least one titanate compound. However, it will be appreciated by one skilled in the art that other catalysts known to those skilled in the art may be equally utilized in the ethylene oligomerization reaction and the AFA co-catalyst injection system 5. For example, catalyst systems based on transition metal complexes such as nickel, chromium, zirconium, or other metal complexes may be used in addition to or as a substitute for the discussed titanate compound.

With reference to FIG. 2 again, a schematic of the antifouling feed stream 40 into the reactor 10 is provided. The at least one AFA co-catalyst is formulated from a combination of the at least one co-catalyst and the at least one antifouling agent via an inline mixer 54 provided with feeds of the co-catalyst and the antifouling agent. In one or more embodiments, the co-catalyst is provided to the inline mixer 54 by a second pump 36b or other locomotion means and the antifouling agent is provided to the inline mixer 54 by a third pump 36c or other locomotion means. The second pump 36b and the third pump 36c providing the locomotive force to convey the combined product of the inline mixer (antifouling feed stream 40) into the reactor 10. The second pump 36b and third pump 36c or other locomotion means for each of the co-catalyst and antifouling agent respectively allows each to be provided at a quantitative measure (weight, volume, concentration) which may be changed or varied independently based on the process conditions over time.

In various embodiments, the inline mixer 54 may be an impeller mixer or a static mixer with internal mixing elements. The inline mixer 54 may include one or more internal mixing elements with a helical, ribbon-like, or plater type geometry. The internal mixing elements provide a method for delivering two streams of fluid into the static mixer which are continuously blended by the non-moving mixing elements during passage of the two streams through the static mixer. As such, it will be appreciated that a stream of the co-catalyst and a stream of the antifouling agent may be provided to the inline mixer 54 and be ejected as the antifouling feed stream 40 comprising the AFA co-catalyst without the need for storing a pre-batch mixture comprising the AFA co-catalyst. The inline mixer 54 also provides the ability to combine three or more streams comprising one or more antifouling agents in combination with the co-catalyst depending on the desired AFA co-catalyst for formation.

In one or more embodiments, the at least one antifouling agent is brought into contact with the at least one co-catalyst at an appropriate ratio for the current process conditions in the inline mixer 54 to form the antifouling feed stream 40 comprising a mixture of the at least one AFA co-catalyst and residual co-catalyst or antifouling agent if provided in excess. The reaction of the antifouling agent and co-catalyst to form the AFA co-catalyst varies based on the specific structure of the antifouling agent. For example, when the antifouling agent is an alcohol, the reaction includes protonolysis of the alkyl group of the co-catalyst. The reaction of forming the AFA co-catalyst from the antifouling agent and the co-catalyst may result in the formation of gas, which may be vented downstream of the inline mixer 54 as an off-gas stream 46 or from the reactor 10. The specific gas generated for discharge as the off gas stream 46 varies depending on the structure of the co-catalyst. For example, triethylaluminum generates ethane gas during the AFA co-catalyst formation. The antifouling feed stream 40 resulting from the mixture of the antifouling agent and co-catalyst is provided to the reactor 10 as a separate injection from the catalyst. Without wishing to be bound by theory, it is believed providing the AFA co-catalyst and the catalyst as a combined stream can cause undesirable increase in fouling and should be avoided.

In various embodiments, the at least one antifouling agent and co-catalyst are mixed in the inline mixer 54 at ratios of antifouling agent to co-catalyst ranging from 0:1 to 1:0 alternatively indicated as ranging from 100% antifouling agent to 100% co-catalyst.

Combining the at least one antifouling agent and the at least one co-catalyst inline at the time of introduction to the reactor provides flexibility in the amount of antifouling agent and co-catalyst reacted to from the AFA co-catalyst. The desired quantitative measure of AFA co-catalyst may be formed by limiting the amount of antifouling agent or co-catalyst introduced to the inline mixer 54. Excess antifouling agent or co-catalyst introduced to the inline mixer 54 beyond that which reacts with the other species is introduced into the reactor 10 along with the formed AFA co-catalyst. For example, if excess co-catalyst is introduced to the inline mixer 54, the product fed to the reactor 10 would comprise the formed AFA co-catalyst along with the residual co-catalyst. The feed of the antifouling agent to the inline mixer 54 can be cut off or adjusted and only the co-catalyst or desired level of formed AFA co-catalyst injected into the reactor 10.

In operation, in one or more embodiments, the level of AFA co-catalyst introduced into the reactor may be minimized during certain processing steps. For example, AFA co-catalyst is useful to activate ethylene oligomerization catalyst (catalyst), but also may undesirably passivate the reactor during fresh reaction start up. The concentration level of AFA co-catalyst may be minimized during reaction start up to avoid passivation of the reactor by introducing a reduced percentage of antifouling agent compared to normal operation thereby generating less AFA co-catalyst while maintaining flow of the co-catalyst. Once the desired AFA co-catalyst concentration has been reached during the reaction startup, the feed of antifouling agent can be terminated to the inline mixer 54 to preclude the introduction of further AFA co-catalyst until warranted. Similarly, the concentration level of AFA co-catalyst may also be reduced during heat exchanger integration to avoid passivation of the heat exchangers.

In operation, in one or more embodiments, the level of co-catalyst introduced into the reactor may be increased during certain process conditions. For example, in a reactor condition where the reaction is lost due to contaminations, heat exchanger integrations, or combinations thereof, the concentration of the co-catalyst in the reactor must typically be increased. The inline mixer 54 of separate stream of co-catalyst and antifouling agent allows for an increase in the co-catalyst provided to the reactor while maintaining or reducing the total formation of AFA co-catalyst subsequently provided to the reactor. Maintaining or reducing the antifouling agent fed to the inline mixer 54 has a commensurate effect on the total production of AFA co-catalyst regardless of any increase in the provision of co-catalyst to the inline mixer 54. This adjustable AFA co-catalyst production afforded by the inline mixer 54 prevents a AFA co-catalyst build up in the reactor to undesired levels as a result of the necessary increased co-catalyst provision to restart the ethylene dimerization reaction. Without wishing to be bound by theory, it is believed the AFA co-catalyst has a maximum efficacy in a range of 1 to 10 parts per million (ppm).

Elevated AFA co-catalyst levels may also lead to additional complications with the reaction system 5. Specifically, an elevated. AFA co-catalyst concentration may increase the difficulty in removing fouling polymers deposited on the reactors and heat exchangers as well as change the nature of the formed polymer.

As commercially available antifouling agents may contain water, the antifouling agent is passed through a drying bed 52 to remove or reduce the water content in the antifouling agent. The dried antifouling agent is subsequently provided to an antifouling agent feed tank 44 to store the dried antifouling agent until demanded for mixing vessel 44 with the co-catalyst in the inline mixer 54. In one or more embodiments, the water content in the antifouling agent provided to the antifouling agent feed tank 44 is maintained lower than approximately 0.3 weight % (wt %) since an excessive amount of water could deactivate the antifouling catalyst system 5. In further embodiments, the water content in the antifouling agent is maintained lower than approximately 0.1 wt %. The drying beds 52 contain a drying agent to remove water from the antifouling agent make-up stream 60. In various embodiments the drying agent is molecular sieves or sodium (Na) supported on alumina or silica. It will be appreciated by one skilled in the art that other means of drying the antifouling agent are known and they are equally envisioned.

In one or more embodiments, the antifouling agent feed tank 44 comprises a pressure relief valve 48. The pressure relief valve 48 is operational to allow the antifouling agent feed tank 44 to vent in the event of excessive pressurization. To avoid rupture of the antifouling agent feed tank 44, the pressure relief valve 48 may allow quickened venting of the antifouling agent feed tank 44 in the event of excessive off-gas formation or insufficient off-gas collection or venting through typical means.

As described previously in this disclosure, embodiments of the described antifouling catalyst systems may comprise one or more titanate compounds. The titanate compounds serve as the catalyst. While several titanate compounds may be included in the antifouling catalyst system, in some embodiments a single titanate compound may be included in the antifouling catalyst system. In one or more embodiments, the titanate compound may be an alkyl orthotitanate. An alkyl orthotitanate has the structure $Ti(OR)_4$ in which R is independently at each occurrence a linear, branched, or cyclic alkyl group. In one or more embodiments, each alkyl group may comprise from 2 to 8 carbon atoms, where each R group may be the same or different. Suitable alkyl titanates may include tetraethyl orthotitanate, tetraisopropyl orthotitanate, tetra-n-butyl orthotitanate (sometimes referred to as titanium butoxide), and tetra-2-ethylhexyl orthotitanate in one or more embodiments, the titanate compound of the antifouling catalyst system consists of tetra-n-butyl orthotitanate.

As also described previously in this disclosure, embodiments of the described antifouling catalyst systems may comprise one or more aluminum alkyl compounds. The aluminum alkyl compounds serve as the co-catalyst and are combined with the antifouling agent to form the AFA co-catalyst. The aluminum alkyl compounds may have a structure of $AlR'_3$ or $AlR'_2H$, where R' is a linear, branched, or cyclic alkyl group comprising from 1 to 20 carbon atoms, or an aluminoxane structure, that is, a partial hydrolysate of trialkylaluminum compounds. It will be appreciated that each R' may be unique providing a formula of AlR'1R'2R'3. For example, and not by way of limitation, suitable aluminum alkyl compounds may include trialkylaluminums. The trialkylaluminums may be trimethylaluminum (TMA), triethylalutninum (TEAL), tripropylaluminum, triisobutylaluminum (TIBAL), trihexylaluminum, trioctylaluminum, or methylaluminoxane (MAO). In one or more embodiments, the aluminum alkyl compound of the antifouling catalyst system consists of triethylaluminum.

Throughout this disclosure the discussed co-catalyst is an aluminum alkyl compound, and more specifically triethylatuminum (TEAL). However, it will be appreciated by one skilled in the art that other co-catalysts may be equally utilized in the formulation of the AFA co-catalyst. For example, methylaluminoxane (MAO), trimethylaluminum, triisobutylaluminum, trioctylaluminum, or combinations thereof may be used in addition to or as a substitute for the discussed aluminum alkyl compound.

In one or more embodiments, the antifouling agent to be combined with the aluminum alkyl compound to form the AFA co-catalyst may be selected from one or more of a phosphonium ($[R1R2R3R4]^+$), sulfonium ($[ROSO_2]^-$), sulfonate ($[R1R2R3S]^+$), and a fouling-preventing surfactant including nonionic surfactants, anionic surfactants, cationic surfactants, and zwitterionic surfactants. Examples of nonionic surfactants include polyoxyethylene monoalkyl ethers $(CH_3(CH_2)_{3-27}(OC_2H_4)_{1-25}OH)$, polyoxyethylene dialkyl ethers $(CH_3(CH_2)_{3-27}(OC_2H_4)_{1-25}O(CH_2)_{3-27}CH_3)$, polyoxypropylene monoalkyl ethers $(CH_3(CH_2)_{3-29}(OC_3H_6)_{1-25}OH)$, polyoxypropylene dialkyl ethers $(CH_3(CH_2)_{3-27}(OC_3H_6)_{1-25}O(CH_2)_{3-27}CH_3)$, polyoxyethylene-polyoxypropylene-polyoxyethylene block copolymers $(HO(C_2H_4O)_{1-25}(C_3H_6O)_{1-25}(C_2H_4O)_{1-25}H)$, polyoxypropylene-polyoxyethylene-polyoxypropylene block copolymers $(HO(C_3H_6O)_{1-25}(C_2H_4O)_{1-25}(C_3H_6O)_{1-25}H)$, oligoglucoside monoalkyl ethers $(CH_3(CH_2)_{3-27}(OC_6H_{10}O_5)_{1-3}OH)$, polyoxyethylene mono(alkylphenyl) ethers $(CH_3(CH_2)_{3-27}(C_6H_4)(OC_2H_4)_{1-25}OH)$, glycerol alkyl esters, N,N,N',N'-tetra(polyoxyalkylene)-1,2-ethylenediamines $((H(O(CH_2)_{2-3})_{1-25})_2NCH_2CH_2N(((CH_2)_{2-3}O)_{1-25}H)_2)$, and polyoxyethylene sorbitan alkyl esters such as polysorbate. Examples of anionic surfactants include sodium stearate and sodium 4-(5-dodecyl) benzenesulfonate. Examples of cationic surfactants include dimethyldioctadecylammonium chloride and dimethyldioctadecylammonium bromide. Examples of zwitterionic surfactants include 3-[(3-cholamidopropyl)dimethylammonio]-1-propanesulfonate, cocamidopropyl hydroxysultaine, cocamidopropyl betaine, and phosphatidylethanolamine.

The antifouling catalyst systems may comprise one or more AFA co-catalysts or derivatives thereof. As used herein, a derivative refers to a derivative structure of an AFA co-catalyst, such as a dimer, trimer, oligomer, polymer, isomer, hydrolysate of an AFA co-catalyst described in this disclosure. It will be appreciated that differing antifouling agents will form differing AFA co-catalysts when combined with the aluminum alkyl compounds. In one or more embodiments, an AFA co-catalyst may comprise a central aluminum molecule bonded to all three of a first chemical group R1, a second chemical group R2, and a third chemical group R3. Chemical Structure #1 depicts a generalized chemical structure of an AFA co-catalyst with R1, R2, and R3 representing antifouling groups, which are derived from the antifouling agent.

Chemical Structure #1

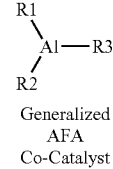

Generalized
AFA
Co-Catalyst

In one or more embodiments, one or more of R1, R2, and R3 are antifouling groups comprising the structure —$O((CH_2)_nO)_mR4$, where n is an integer of from 1 to 20. In various embodiments, n is an integer of from 1 to 10, 1 to 5, or 2 to 3, m is an integer of from 1 to 100, and R4 is a hydrocarbyl group. In various embodiments, n is an integer of from 1 to 10, 1 to 5, or 2 to 3 and m is an integer of from 1 to 50, 1 to 20, or 1 to 10. The structure of the antifouling group, —$O((CH_2)_nO)_mR4$, is depicted in Chemical Structure #2. The central aluminum atom is bonded to a terminal oxygen of the antifouling group opposite to the R4 hydrocarbyl group. As used throughout this disclosure, a hydrocarbyl group refers to a chemical group that consists of hydrogen and carbon atoms. For example, a hydrocarbyl group may be linear, branched, or cyclic, and may comprise one or more alkyl moieties, one or more alkenyl moieties, one or more alkynyl moieties, aryl moieties, or combinations thereof. In various embodiments, R4 may be a hydrocarbyl group having from 1 to 100 carbon atoms, from 2 to 50 carbon atoms, or from 8 to 28 carbon atoms.

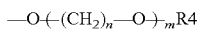

Chemical Structure #2—Antifouling Group

As previously described in this disclosure, one, two, or all three of R1, R2, and R3 may comprise the antifouling groups comprising the structure of Chemical Structure #2. In embodiments described in this disclosure, the chemical groups R1, R2, or R3 that do not comprise the antifouling group, if any, are hydrocarbyl groups. For example, R1 may be an antifouling group with the structure depicted in Chemical Structure #2 and R2 and R3 may be hydrocarbyl groups. In another embodiment, R1 and R2 may be antifouling groups with the structure depicted in Chemical Structure #2, and R3 may be a hydrocarbyl group. In another embodiment, R1, R2, and R3 may be antifouling groups with the structure depicted in Chemical Structure #2. When at least two of R1, R2, and R3 are hydrocarbyl groups, they may be identical to one another or may be different hydrocarbyl groups. Also, when two or more of R1, R2, or R3 are antifouling groups, the antifouling groups may be identical or chemically different. However, they will each have the generic structure depicted in Chemical Structure #2. In various embodiments, R1, R2 and R3 that are hydrocarbyl groups may each have from 1 to 100 carbon atoms, from 2 to 75 carbon atoms, or from 2 to 50 carbon atoms. For example, if R1, R2, or R3 are hydrocarbyl groups, they may be linear alkyl groups such as methyl, ethyl, propyl, or butyl groups, or branched alkyl groups such as isopropyl or isobutyl groups.

By way of example, if R1 is an antifouling group, and R2 and R3 are hydrocarbyl groups, the generalized structure of the AFA co-catalyst can be represented by Chemical Structure #3.

Chemical Structure #3

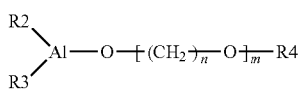

Example of Generalized AFA
Co-Catalyst

In one or more embodiments, the AFA co-catalyst may comprise an R1 group that is an ethyl group, an R2 group that is an ethyl group, and an R3 that is an antifouling group having the structure —O((CH$_2$)$_n$O)$_m$R4, where n=2, m=4, and R4 is a dodecyl group. Such an AFA co-catalyst can be written as (CH$_3$CH$_2$)$_2$AlO(CE$_2$CH$_2$O)$_4$(CH$_2$)$_{11}$CH$_3$, and has the chemical structure depicted in Chemical Structure #4, where "Et" represents an ethyl group.

Chemical Structure #4

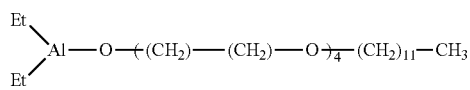

Example of AFA Co-Catalyst

In one or more embodiments, the AFA co-catalyst may be present as a dimerized form, referred to herein as an example of a derivative of an AFA co-catalyst. A prepared AFA co-catalyst may be present in both dimerized and non-dimerized, that is, non-bonded, form. For example, in a dimerized state, the AFA co-catalyst may comprise a structure as shown in Chemical Structure #5. Chemical Structure #5 shows the dimerized embodiment of the AFA co-catalyst structure depicted in Chemical Structure #3. In a dimerized embodiment, bonds may form between the central aluminum atoms of an AFA co-catalyst molecule and an oxygen atom of a neighboring AFA co-catalyst molecule. It should be understood that while in Chemical Structure #5 the central aluminum atoms are bonded to the oxygen atom in the neighboring AFA co-catalyst that is the nearest to its central aluminum atom, in other embodiments, this may not be the case, and the a central aluminum atom may bond with an oxygen atom of a neighboring AFA co-catalyst which is not the nearest to its central aluminum atom.

Chemical Structure #5

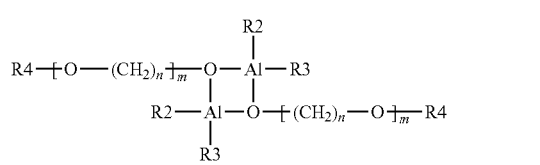

Example of Dimerized AFA Co-Catalyst

In one or more embodiments, the AFA co-catalyst may be present in different isomer states, one such example depicted in Chemical Structure #6. An isomer is an example of a derivative structure of an AEA co-catalyst. For example, and as depicted in Chemical Structure #6, the central aluminum atom of an AFA co-catalyst may be bonded to two oxygen atoms of a single antifouling group to form a chelate ring. It should be understood that while Chemical Structure #6 depicts an isomer where the two oxygen atoms nearest to the central aluminum atom are bonded with the central aluminum atom, in other embodiments other isomers may form, such as an isomer formed when the central aluminum atom forms a bond with an oxygen atom which is not as close as another oxygen atom to the central aluminum atom in the AFA co-catalyst molecule. For example, while Chemical Structure #6 shows a ring structure with two oxygen atoms and n carbon atoms, larger ring structures may form in other isomers, such as rings having three or more oxygen atoms. It should be understood that isomers of the AFA co-catalyst described, such as that shown in Chemical Structure #6, are considered AFA co-catalyst and fit into the base structure depicted in Chemical Structure #1. For instance, the existence of two oxygen atoms bonded to the central aluminum atom, where both oxygen atoms are part of an antifouling group, is considered to conform to the base structure depicted in Chemical Structure #1.

Chemical Structure #6

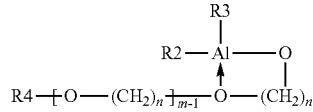

Example of Isomer of AFA
Co-Catalyst

Each of Chemical Structures #3-#6 illustrates the AFA co-catalyst with the antifouling group of Chemical Structure #2. It will be appreciated that in various embodiments, other or additional antifouling groups may be bonded at R1, R2, or R3 to the central aluminum atom of the generalized AFA co-catalyst of Chemical Structure #1. Specific, non-limiting, additional examples for the antifouling group include the structures such as —NHR, —OC(O)R, and —OS(O)OR.

Additionally, the AFA co-catalysts may be aluminum complexes formed by the reactions of AlR1R2R3 (Chemical Structure #1) and an ionic surfactant. The resulting AFA co-catalysts are structurally as illustrated in Chemical Structure #7, where R4 and X+ represent the anionic and cationic parts of an ionic surfactant, respectively.

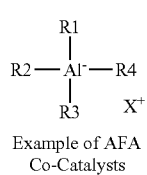

Chemical Structure #7

Example of AFA Co-Catalysts

In one or more embodiments, the antifouling catalyst system comprises one or more phosphonium antifouling agent. The phosphonium antifouling agent may be combined with the aluminum alkyl compound to form the AFA co-catalyst depicted in Chemical Structure #7. As used in this disclosure, phosphonium antifouling agents include any compound comprising the phosphonium structure depicted in Chemical Structure 48, where $R_1$, $R_2$, $R_3$, and $R_4$ represents chemical groups which may contain other moieties, and the various R groups may be identical or different from one another. Generally, phosphonium antifouling agents may be introduced into the antifouling catalyst system as phosphonium salts, where the phosphonium cation forms an ionic bond with an anion compound. As used in this disclosure, phosphonium antifouling agents include phosphonium salts or zwitterionic compounds comprising phosphonium moieties.

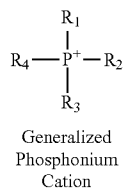

Chemical Structure #8

Generalized Phosphonium Cation le;2qSuitable phosphonium antifouling agents include, without limitation, tetraalkyl phosphonium salts. For example, the antifouling agent may include tetraalkyl phosphonium halides (such as tetrahutyl phosphonium halide), phosphonium malonates (such as tetrabutylphosphonium malonate), trihexyltetradecylphsophonium halides (such as trihexyltetradecylphsophonium bromide), tetrabutylphosphonium halides (such as tetrabutylphosphonium iodide), tetrabutylphosphonium tetrahaloborates (such as tetrabutylphosphonium tetrafluoroborate), tetrabutylphosphonium halides (such as tetrabutylphosphonium chloride), tetrahutylphosphonium hexahalophosphates (such as tetrabutylphosphonium hexafluorophosphate), or tetrabutylphosphonium tetrahaloborates (such as tetrabutylphosphonium tetrafluoroborate). As used throughout this disclosure, a halide may include fluoride, chloride, bromide, or iodide (and "halo" may include the elements fluorine, chlorine, bromine, or iodine). In one or more embodiments, the groups, that is, $R_1$, $R_2$, $R_3$, and $R_4$, may be linear, branched, or cyclic alkyls, alkenyls, alkynyls, or aryls, and the R groups may be identical or different from one another.

In one or more embodiments, the antifouling catalyst system comprises one or more sulfonate antifouling agents. The sulfonate antifouling agent may be combined with the aluminum alkyl compound to form the AFA co-catalyst depicted in Chemical Structure #7. As used in this disclosure, sulfonate antifouling agents include any compound comprising the structure depicted in Chemical Structure #9, where R represents a chemical group which may contain other moieties. Generally, sulfonate antifouling agents may be introduced into the antifouling catalyst system as a sulfonate salt, where the sulfonate anion forms an ionic bond with a cation compound. As used in this disclosure, sulfonate antifouling agents include sulfonate salts or zwitterionic compounds comprising sulfonate moieties.

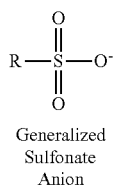

Chemical Structure #9

Generalized Sulfonate Anion

Suitable sulfonate antifouling agents include, without limitation, sulfonate salts. For example, sulfonate antifouling agents may include, without limitation, sodium dodecylbenzenesulfonate, sodium dioctylsulfonsuccinate, tetrabutylphosphonium methanesulfonate, tetrabutylphosphonium p-toluenesulfonate, and (hexadecyl) trimethylammonium, p-toluenesulfonate. In other embodiments, suitable antifouling agents may include non-salt sulfonates, that is, zwitterionic sulfonates which do not dissociate into a separated cation and anion. For example, non-salt sulfonates suitable as antifouling agents include, without limitation, 3-(dimethyl(octadecyl)ammonio)propane-1-sulfonate, 3,3'-(1,4-didodecylpiperazine-1,4-diium-1,4-diyl)bis(propane-1-sulfonate), and 3-(4-(tert-butyl)pyridinio)-1-propanesulfonate.

In one or more embodiments, the antifouling catalyst system comprises one or more sulfonium antifouling agents. The sulfonium antifouling agent may be combined with the aluminum alkyl compound to form the AFA co-catalyst depicted in Chemical Structure 47, Sulfonium antifouling agents are generally depicted in Chemical Structure #10, where $R_1$, $R_2$, and $R_3$ represent chemical groups which may contain other moieties, and the various R groups, that is, $R_1$, $R_2$, and $R_3$, may be identical or different from one another. Generally, sulfonium antifouling agents may be introduced into the antifouling catalyst system as sulfonium salts, where the sulfonium cation forms an ionic bond with an anion compound. As used in this disclosure, sulfonium antifouling agents include sulfonium salts or zwitterionic compounds comprising sulfonium moieties.

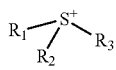

Chemical Structure #10

Generalized
Sulfonium
Cation

In one or more embodiments, the antifouling catalyst systems may comprise more than one molecular species of AFA co-catalyst. For example, some AFA co-catalysts may comprise one, two or three antifouling groups, while others comprise a different number of antifouling groups. The mixture of these AFA co-catalyst species may form a bulk AFA co-catalyst which can be characterized by its bulk molar ratio of hydrocarbyl groups to antifouling groups which are attached to the central aluminum atoms, respectively. For example, if half of the AFA co-catalyst has one antifouling group and two hydrocarbyl groups, and, the other half of the AFA co-catalyst has two antifouling groups and one hydrocarbyl group, then the bulk molar ratio of hydrocarbyl groups to antifouling groups would be 1:1 because there is a bulk equal amount of hydrocarbyl groups to antifouling groups. In various embodiments, the bulk molar ratio of hydrocarbyl groups to antifouling groups may be from be from 1:3 to 2:1, 1:2 to 2:1, or from 1:1 to 2:1.

In one or more embodiments, the antifouling catalyst system may comprise one or more ether compounds to reduce the formation of polymers. The one or more ether compounds may include cyclic ethers such as, but not limited to, tetrahydroffiran (THF), 1,4-dioxane, tetrahydropyran (THP), or combinations thereof.

The antifouling catalyst systems may comprise at least one or more titanate compounds, one or more aluminum alkyl compounds, and one or more AFA co-catalysts. In various, the molar ratio of total titanate compounds to total aluminum alkyl compounds may be from 1:10 to 1:1.5, from 1:3 to 1:1.5, or from 1:3 to 1:2.

In various embodiments, the molar ratio of the antifouling agents brought into contact with the aluminum alkyl compound to the sum of the aluminum alkyl compounds brought into contact with the aluminum alkyl compound and additionally provided into the reactor may be from 0.001:1 to 0.5:1, from 0.01 to 0.18, or from 0.01 to 0.13.

In various embodiments, the molar ratio of total titanate compounds to total ether compounds may be from 1:20 to 1:0, from 1:10 to 1:1, or from 1:8 to 1:3.

It should be understood that the molar ratios of components of the antifouling catalyst systems described previously are representative of the total amount of each component of the antifouling catalyst system relative to the total amount of titanate compound or aluminum alkyl compound, where the "total" amount refers to the molar amount of all species of the antifouling catalyst system which may be considered as a particular component type, that is, titanate compound, aluminum alkyl compound, ether compound, or antifouling agent. The total amount of a component may include two or more chemical species which are titanate compounds, aluminum alkyl compounds, ether compounds, or antifouling agents, respectively.

In one or more embodiments, without being bound by theory, it is believed that heteroatoms such as oxygen or nitrogen of the AFA co-catalysts may form weak coordination with the titanate compound utilized as the catalyst in the catalyst system. It is believed that, in one or more embodiments, the alkyl groups or other relatively long-chained groups of the AFA co-catalysts may serve in some capacity to prevent ethylene access to the catalytic center of the titanate compound. The restriction of access of the ethylene to the titanate catalytic site may reduce the polymerization of ethylene and thus reduce reactor fouling.

In one or more embodiments, the introduction of the AFA co-catalyst into the catalyst system may suppress polymer formation while not greatly reducing catalytic activity of 1-butene formation. In one embodiment, polymer formation (fouling) may be reduced by at least 5%, 10%, 20%, 30%, 40%, 50%, 60%, 70%, 80%, 90%, or even 95% by the inclusion of an AFA co-catalyst. In one embodiment, 1-butene production may be increased, stay the same, or may decrease by less than or equal to 50%, 40%, 30%, 20%, 10% or even 5% by the inclusion of an AFA co-catalyst. In some embodiments, AFA co-catalysts may both reduce the polymer formation, such as by at least 5%, 10%, 20%, 30%, 40%, 50%, 60%, 70%, 80%, 90% or even 95%, and increase, not effect, or decrease 1-butene production rate by less than or equal to 50%, 40%, 30%, 20%, 10% or even 5%. Reduction in polymer formation rates and catalytic activity on a percentage basis are based on catalyst systems which include one or more AFA co-catalysts described as compared with catalyst systems which are void of an AFA co-catalyst.

It should now be understood the various aspects of the process for selectively producing 1-butene are described and such aspects may be utilized in conjunction with various other aspects.

In a first aspect, the disclosure provides a process for selectively producing 1-butene. The process comprising the following two steps: Step 1: combining at least one antifouling agent and at least one aluminum alkyl compound to form an antifouling teed stream, wherein bringing the at least one antifouling agent into contact with the at least one aluminum alkyl compound forms at least one antifouling agent co-catalyst comprising the structure:

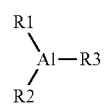

or its dimeric faun, and Step 2: feeding the antifouling feed stream, a catalyst comprising at least one titanate compound, and ethylene into a reactor to dimerize ethylene, wherein the catalyst comprising at least one titanate compound is fed as a stream separated from the antifouling feed stream. The molar ratio of the at least one antifouling agent and the at least one aluminum alkyl compound provided to form the antifouling feed stream may be varied in real-time via an inline mixer to adjust a ratio of the formed antifouling agent co-catalyst and residual aluminum alkyl compound or antifouling agent in the antifouling feed stream.

In a second aspect, the disclosure provides the process of the first aspect, in the molar ratio of the at least one aluminum alkyl compound provided in step 1 to form the antifouling feed stream to the at least one titanate compound provided in Step 2 is equal to or greater than 1.5 and equal to or lower than 3.0.

In a third aspect, the disclosure provides the process of the first or second aspects, in which one or more of the chemical groups R1, R2, and R3 are antifouling groups comprising the structure —O(($CH_2$)$_n$O)$_m$R4, wherein: n is an integer of from 1 to 20; m is an integer of from 1 to 100; and R4 is a hydrocarbyl group. The chemical groups R1, R2, or R3 that do not comprise the antifouling group, if any, are hydrocarbyl groups.

In a fourth aspect, the disclosure provides the process of any of the first through third aspects, in which the inline mixer is configured to allow ratios of antifouling agent to aluminum alkyl compound provided to the inline mixer from 0:1 to 1:0.

In a fifth aspect, the disclosure provides the process of any of the first through fourth aspects, in which the molar ratio of the at least one antifouling agent and the at least one aluminum alkyl compound is equal to or greater than 0.01 and equal to or lesser than 0.18.

In a sixth aspect, the disclosure provides the process of any of the first through fifth aspects, in which a level of antifouling agent co-catalyst introduced into the reactor is reduced during reaction start up to avoid passivation of the reactor by reducing the ratio of antifouling agent to aluminum alkyl compound provided to the inline mixer thereby generating less antifouling agent co-catalyst while maintaining flow of the aluminum alkyl compound to the reactor.

In a seventh aspect, the disclosure provides the process of the sixth aspect, in which the concentration of antifouling agent co-catalyst is monitored during reactor startup and the feed of the antifouling agent to the inline mixer is terminated upon reaching a predetermined concentration of the antifouling agent co-catalyst.

In an eighth aspect, the disclosure provides the process of any of the first through seventh aspects, in which, to recover the dimerization reaction of ethylene in case of reaction loss, a level of the aluminum alkyl compound introduced into the reactor is increased while maintaining or reducing a level of the antifouling agent co-catalyst introduced into the reactor by increasing a flow rate of the aluminum alkyl compound to the antifouling feed stream in combination with maintaining or reducing a flow rate of the antifouling agent to the antifouling feed stream.

In a ninth aspect, the disclosure provides the process of any of the first through fifth aspects, in which the concentration of the antifouling agent co-catalyst in the reactor is maintained at or below 10 ppm by adjusting a ratio of antifouling agent to aluminum alkyl compound provided to the inline mixer and a total flow rate of the antifouling feed stream.

In a tenth aspect, the disclosure provides the process of any of the third through ninth aspects, in which n is from 1 to 5.

In an eleventh aspect, the disclosure provides the process of any of the third through tenth aspects, in which m is from 1 to 20.

In a twelfth aspect, the disclosure provides the process of any of the third through eleventh aspects, in which R4 has from 1 to 100 carbon atoms.

In a thirteenth aspect, the disclosure provides the process of the first or second aspects, in which an atom existing in the chemical groups R1, R2, or R3 binds to the aluminum atom to form a chelate ring.

In a fourteenth aspect, the disclosure provides the process of the first or second aspects, in which one or more of the chemical groups R1, R2, and R3 are antifouling groups comprising a phosphonium moiety.

In a fifteenth aspect, the disclosure provides the process of the fourteenth aspect, in which the antifouling agent comprises one or more of a tetraalkyl phosphonium halide, a phosphonium malonate, a trihexyltetradecylphsophonium halide, a tetrabutylphosphonium halide, a tetrabutylphosphonium tetrahaloborate, a tetrabutylphosphonium halide, a tetrabutylphosphonium hexahalophosphate, and a tetrabutylphosphonium tetrahaloborate.

In sixteenth aspect, the disclosure provides the process of the first or second aspects, in which one or more of the chemical R1, R2, and R3 are antifouling groups comprising a sulfonate moiety.

In a seventeenth aspect, the disclosure provides the process of the sixteenth aspect, in which the antifouling agent comprises one or more of sodium dodecylbenzenesulfonate, sodium dioctylsulfonsuccinate, tetrabutylphosphonium methanesulfonate, tetrabutylphosphonium p-toluenesulfonate, hexadecyltrimethylammonium p-toluenesulfonate, 3-(dimethyl(octadecyl)ammino)propane-1-sulfonate, 3,3'-(1,4-didodecylpiperazine-1,4-diium-1,4-diyl) bis(propane-1-sulfonate), and 3-(4-(tert-butyl)pyridinio-1-propanesulfonate.

In an eighteenth aspect, the disclosure provides the process of the first or second aspects, in which one or more of the chemical groups R1, R2, and R3 are antifouling groups comprising a sulfonium moiety.

It should be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

What is claimed is:

1. A process for selectively producing 1-butene, the process comprising the following two steps:
   Step 1: combining at least one antifouling agent and at least one aluminum alkyl compound to form an antifouling feed stream, wherein bringing the at least one antifouling agent into contact with the at least one aluminum alkyl compound forms at least one antifouling agent co-catalyst comprising the structure:

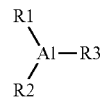

or its dimeric form, wherein one or more of the chemical groups R1, R2, and R3 are antifouling groups comprising the structure —O((CH$_2$)$_n$O)$_m$R4, wherein:
   n is an integer of from 1 to 20;
   m is an integer of from 1 to 100; and
   R4 is a hydrocarbyl group;
   wherein the chemical groups R1, R2, or R3 that do not comprise the antifouling group, if any, are hydrocarbyl groups, and
   Step 2: feeding the antifouling feed stream, a catalyst comprising at least one titanate compound, and ethylene into a reactor and dimerizing ethylene to produce 1-butene, wherein the catalyst comprising at least one titanate compound is fed as a stream separate from the antifouling feed stream;
   wherein a molar ratio of the at least one antifouling agent to the at least one aluminum alkyl compound provided to form the antifouling feed stream is varied in real-time via an inline mixer to adjust a ratio of the formed antifouling agent co-catalyst and residual aluminum alkyl compound or antifouling agent in the antifouling feed stream.

2. The process of claim 1, wherein a molar ratio of the at least one aluminum alkyl compound provided in step 1 to form the antifouling feed stream to the at least one titanate compound provided in Step 2 is equal to or greater than 1.5 and equal to or lower than 3.0.

3. The process of claim 1, wherein the molar ratio of the at least one antifouling agent and the at least one aluminum alkyl compound is equal to or greater than 0.01 and equal to or less than 0.18.

4. The process of claim 1, wherein a level of antifouling agent co-catalyst introduced into the reactor is reduced during reaction start up to avoid passivation of the reactor by reducing the ratio of antifouling agent to aluminum alkyl compound provided to the inline mixer thereby generating less antifouling agent co-catalyst while maintaining flow of the aluminum alkyl compound to the reactor.

5. The process of claim 4, wherein the concentration of antifouling agent co-catalyst is monitored during reactor startup and the feed of the antifouling agent to the inline mixer is terminated upon reaching a predetermined concentration of the antifouling agent co-catalyst.

6. The process of claim 1, wherein a level of the aluminum alkyl compound introduced into the reactor is increased while maintaining or reducing a level of the antifouling agent co-catalyst introduced into the reactor by increasing a flow rate of the aluminum alkyl compound to the antifouling feed stream in combination with maintaining or reducing a flow rate of the antifouling agent to the antifouling feed stream.

7. The process of claim 1, wherein the concentration of the antifouling agent co-catalyst in the reactor is maintained at or below 10 ppm.

8. The process of claim 1, wherein n is from 1 to 5.

9. The process of claim 1, wherein m is from 1 to 20.

10. The process of claim 1, wherein R4 has from 1 to 100 carbon atoms.

11. The process of claim 1, wherein an oxygen existing in the chemical groups R1, R2, or R3 binds to the aluminum atom to form a chelate ring.

* * * * *